(12) United States Patent
Ogier et al.

(10) Patent No.: US 8,663,660 B2
(45) Date of Patent: Mar. 4, 2014

(54) POLYMERIZED MICELLES

(75) Inventors: Julien Ogier, Paris (FR); Eric Doris, Orsay (FR); François Lefoulon, Orléans (FR); Thomas Arnauld, Orléans (FR)

(73) Assignees: Les Laboratories Servier, Suresnes Cedex (FR); Commissariat a l'Energie Atomique, Paris (FR)

( * ) Notice: Subject to any disclaimer, the term of this patent is extended or adjusted under 35 U.S.C. 154(b) by 455 days.

(21) Appl. No.: 12/736,627

(22) PCT Filed: Apr. 28, 2009

(86) PCT No.: PCT/FR2009/000493
§ 371 (c)(1),
(2), (4) Date: Jan. 4, 2011

(87) PCT Pub. No.: WO2009/133325
PCT Pub. Date: Nov. 5, 2009

(65) Prior Publication Data
US 2011/0105516 A1    May 5, 2011

(30) Foreign Application Priority Data

Apr. 29, 2008    (FR) ..................... 08 02390

(51) Int. Cl.
*A61K 9/00*    (2006.01)
*A61K 47/32*    (2006.01)
*A61K 47/36*    (2006.01)

(52) U.S. Cl.
USPC ............... 424/400; 526/72; 526/89; 526/274; 526/277; 526/285; 526/286; 526/287; 526/288; 526/304; 526/307; 526/307.4; 526/312; 526/335

(58) Field of Classification Search
USPC ............ 526/72, 89, 274, 277, 285, 286, 287, 526/288, 304, 307, 307.4, 312, 335
See application file for complete search history.

(56) References Cited

U.S. PATENT DOCUMENTS

| | | | |
|---|---|---|---|
| 2002/0064513 A1 | 5/2002 | Maitra et al. | |
| 2003/0133972 A1* | 7/2003 | Danthi et al. | ................. 424/450 |
| 2005/0277739 A1* | 12/2005 | Yang et al. | .................... 525/242 |

OTHER PUBLICATIONS

Hamid et al. (British Polymer Journal, vol. 16, Published Mar. 1984, p. 39-45).*
Gotto, et al., "Micellar Behaviour of Sugar-Carrying Polystyrene in Aqueous Solution" Marcomol. Chem. Phys., vol. 202, No. 7, p. 1161-1165, 2001.
International Search Report for PCT/FR2009/000493 of Dec. 1, 2009.

* cited by examiner

*Primary Examiner* — Richard Schnizer
*Assistant Examiner* — Alma Pipic
(74) *Attorney, Agent, or Firm* — Hueschen and Sage

(57) ABSTRACT

Polymerized micelles comprising polymerized amphiphilic molecules obtained starting from amphiphilic molecules having one or two lipid chains each comprising one or two polymerizable moieties and linked to a polar head.

18 Claims, 9 Drawing Sheets

Scheme 4:

POLYMERIZED MICELLES

The invention relates to polymerised micelles, to processes for the preparation thereof and to applications thereof.

BACKGROUND

A large number of molecules having therapeutic activity, and especially anti-cancer molecules, have low solubility in water, owing to the intrinsic hydrophobic properties of the molecule. A certain level of hydrophobicity is in fact necessary for these molecules, in order to enable them to be internalised by cells. Vectorisation of therapeutic molecules is aimed at circumventing the problems associated with, especially, the solubility, stability, pharmacokinetics and biodistribution of said molecules and specifically targeting them.

Various vectorisation systems for hydrophobic compounds have been described in the literature as being capable of transporting sufficient amounts of molecules having therapeutic activity through the various biological barriers in order to efficaciously reach their site of action.

One of those vectorisation techniques consists of encapsulating an active ingredient in a microsphere formed by a matrix of polymers such as poly(alkylcyanoacrylates), poly (anhydrides) and polylactic acid). Those microspheres have sizes of from 20 µm to 100 µm, which rules out their use by the intravenous route and allows relatively low levels of inclusion of hydrophobic compounds of between 0.2% and 3.5%.

Polymer micelles, another vectorisation technique, denote colloidal dispersions composed of amphiphilic polymers having separate hydrophilic and hydrophobic regions. These polymer micelles are supramolecular core/shell structures. Polymer micelles are composed of polyethers used in combination with poly(ethylene glycol) in order to form amphiphilic polymers in the form of diblock copolymers (pluronics: PPO-co-PEG) or triblock copolymers (poloxamers: PEG-co-PPO-co-PEG). Those polymer micelles have a size between 50 nm and 100 nm. The inclusion levels of compounds in the polymer micelles are between 0.1% and 40%, inclusive, depending on the inclusion method used: inclusion by evaporation, inclusion by dialysis or inclusion by nanoprecipitation. Polymer micelles are accordingly vectors which allow large amounts of hydrophobic compounds to be incorporated but which require a difficult industrial and technical formation technique (synthesis and inclusion).

Vectorisation systems using liposomes and vesicles of polymers are the object of intensive research and a number of formulations of medicaments using these systems are currently undergoing clinical trials, some of them even having been approved for clinical use. Liposomes and vesicles of polymers may include hydrophilic active ingredients in the aqueous core of the vesicle or hydrophobic molecules in the polymer bilayer. Liposomes and vesicles of polymers have very varied structures (multi-lamellar vesicles MLV, small uni-lamellar vesicles SUV, large uni-lamellar vesicles LUV, giant vesicles GUV) and very varied sizes between 100 nm and 1000 nm, inclusive. Liposomes and vesicles of polymers are important active ingredient vehicles in the vectorisation of hydrophilic molecules.

In 2003, a new type of organisation on the surface of carbon nanotubes was discovered: nano-rings, i.e. a structuring of amphiphilics into rings over the entire length of the nanotubes. Nano-rings are rings of polymerised surfactants formed on the surface of the nanotubes and then separated from their carbon support in order to be used as solubilisation agents for hydrophobic active ingredients (WO 2004/092231). Nano-rings are, however, nano-vectors that are difficult to industrialize.

The above-described delivery vectors meet the challenge of vectorisation more or less well, which is to transport sufficient amounts of active ingredient in efficacious manner and with low toxicity in order to treat the pathology. These vectors remedy the problem of the solubility of hydrophobic active ingredients but without resolving the problems of vector size, formation and industrialization. The present invention is accordingly aimed at proposing a new strategy in order to obtain nano-vectors having a capability for inclusion of hydrophobic active ingredients that is greater than that of customary vectors in the literature and having a simple formulation facilitating their future industrialization.

SUMMARY OF THE INVENTION

The present invention relates to polymerised micelles characterised in that they comprise polymerised amphiphilic molecules obtained starting from amphiphilic molecules having one or two lipid chains each comprising one or two polymerisable moieties, of the diacetylene, vinyl, acrylate or styrene type, and linked to a polar head.

BRIEF DESCRIPTION OF THE DRAWINGS

The present invention is illustrated by the following Figures, without being limited thereby.

DETAILED DESCRIPTION

Figure 1:
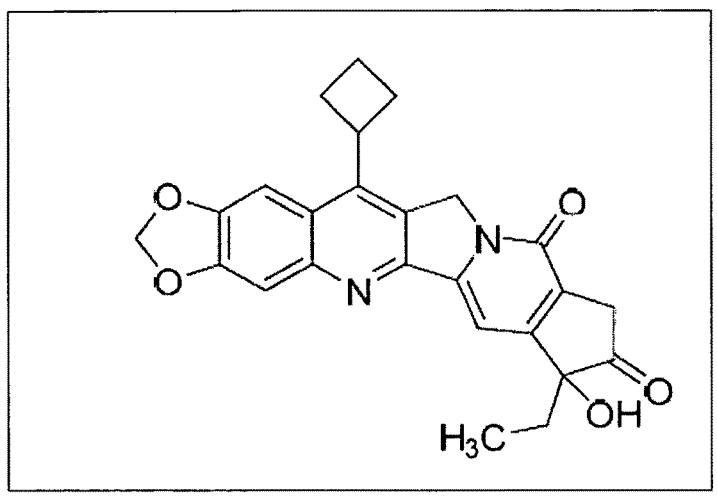
FIG. 1: Chemical structure of S39625.

In accordance with the present invention, "micelles" are understood to be self-assembled spherical objects having a hydrophilic surface and a lipophilic core and whose size is less than 100 nm.

"Amphiphilics" or "surfactants" are understood to be organic molecules having the feature of being simultaneously hydrophilic and hydrophobic. Amphiphilics, characterised by their antagonist properties, have particular properties in solution and organise themselves spontaneously in aqueous media into various microstructures.

The invention relates preferably to polymerised micelles comprising polymerised amphiphilic molecules obtained starting from amphiphilic molecules of general formula

A-X—B-L-Z wherein A represents $CH_3—(CH_2)_m—C≡C—C≡C—(CH_2)_n—$ or $CH_2=CH—$ or $CH_2=CH—C_6H_4—$, n and m, which may be the same or different, being integers from 1 to 16;

wherein X represents CO—NH or NH—CO or a bond, X is a bond if B is a bond and L is a bond;

wherein B represents $—(CH_2)_m—C≡C—C≡—C(CH_2)_n—$ or $—CH=CH—C_6H_4—$ or a bond, n and m, which may be the same or different, being integers from 1 to 16;

wherein L represents $—(CH_2)_r—CH[NH—CO-A']—$ or a bond, r being an integer from 1 to 16, and A' represents A;

wherein Z represents $$—CONH—(CH_2)_s—CH(R_1)—N(CH_2—R_2)(CH_2—R_2)$$

or $$—NHCO—(CH_2)_s—CH(R_1)—N(CH_2—R_2)(CH_2—R_2),$$

s being an integer from 1 to 16, with $R_2$ representing COOH or $SO_3H$ or $OSO_3H$ or $OPO_3H_2$ or $OPO_2H_2$, with $R_1$ representing H or a radical COOH or $SO_3H$ or $OSO_3H$ or $OPO_3H_2$ or $OPO_2H_2$ or a group $—CO—NH—(CH_2)_t—CH_3$, t being an integer from 1 to 16, or Z may also be a neutral hydrophilic polar head of the sugar or polysaccharide type, and also addition salts thereof with a pharmaceutically acceptable acid or base.

Among the pharmaceutically acceptable acids there may be mentioned, without implying any limitation, hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid, camphoric acid.

Among the pharmaceutically acceptable bases there may be mentioned, without implying any limitation, sodium hydroxide, potassium hydroxide, triethylamine, tert-butylamine.

The invention relates preferably to polymerised micelles comprising polymerised amphiphilic molecules obtained starting from amphiphilic molecules of general formula

A-X—B-L-Z wherein A represents $CH_3—(CH_2)_m—C≡C—C≡C—(CH_2)_n—$, n and m, which may be the same or different, being integers from 1 to 16;

wherein X represents CO—NH or NH—CO or a bond, X is a bond if B is a bond and L is a bond;

wherein B represents $—(CH_2)_m—C≡C—C≡—(CH_2)_n—$ or a bond, n and m, which may be the same or different, being integers from 1 to 16;

wherein L represents $—(CH_2)_r—CH[NH—CO-A']—$ or a bond, r being an integer from 1 to 16, and A' represents A or $CH_2=CH—$ or $CH_2=CH—C_6H_4—$;

wherein Z represents $$—NHCO—(CH_2)_s—CH(R_1)—N(CH_2—COOH)(CH_2—COOH)$$

or $$—CONH—(CH_2)_s—CH(R_1)—N(CH_2—COOH)(CH_2—COOH),$$

s being an integer from 1 to 16, with $R_1$ representing H or a radical COOH or a group $—CO—NH—(CH_2)_t—CH_3$, t being an integer from 1 to 16, or Z may also be a neutral hydrophilic polar head of the sugar or polysaccharide type, and also addition salts thereof with a pharmaceutically acceptable acid or base.

The invention relates also to polymerised micelles composed of amphiphilic molecules whose neutral hydrophilic polar heads are of the crown ether type.

The invention relates advantageously to polymerised micelles whose polar head Z is functionalised.

"Functionalised" polymerised micelles are understood to be polymerised micelles modified with molecular recognition ligands so as to make them intelligent and selective vectors in order to specifically identify antigens or receptors overexpressed on the surface of target cells such as cancerous or infectious cells. For that purpose, the polymerised micelles must be functionalised by specific ligands, the attachment of which to the surface of the vector is accomplished by chemical coupling.

Advantageously, the ligands attached to the surface of the polymerised micelles are: fluorophores or agents of nuclear imaging ($^{99}Tc$, $^{111}In$, $^{125}I$, $^{18}F$, $^{64}Cu$) or of optical imaging (cyanine, fluorescein, luciferase, quantum dots) or of magnetic imaging (iron oxide particles), folic acid, mannose, galactose, antibodies, RGD-type ligands.

Preferably, the polymerised micelles according to the invention are functionalised at the polar head Z by a folic acid.

In a preferred embodiment, the polymerised micelles are functionalised in accordance with a process as described in Example 5.

Surface functionalisation of the polymerised micelles accordingly provides said polymerised micelles with properties of stealth and allows targeting of specific cells.

The invention relates also to polymerised micelles including one or more hydrophobic compounds within polymerised amphiphilics according to the invention.

"Hydrophobic compounds" are understood to be molecules of small size having low solubility in water of less than 1 g per liter in all or part of the pH range or proteins or nucleic acids having problems of solubility or stability in aqueous media.

Preferably, the polymerised micelles according to the invention are composed of polymerised amphiphilic molecules obtained starting from the amphiphilic molecule II-4 of formula Also preferably, the polymerised micelles are composed of polymerised amphiphilic molecules obtained starting from the amphiphilic molecule II-23 of formula

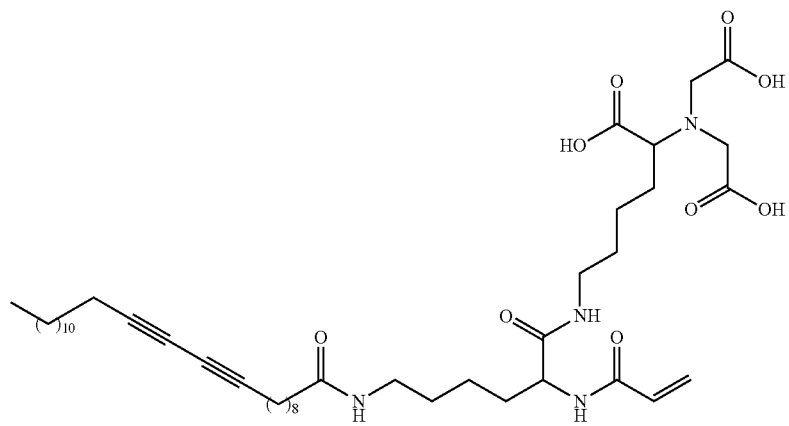

Advantageously, the polymerised micelles according to the invention are composed of polymerised amphiphilic molecules obtained starting from the amphiphilic molecule of formula

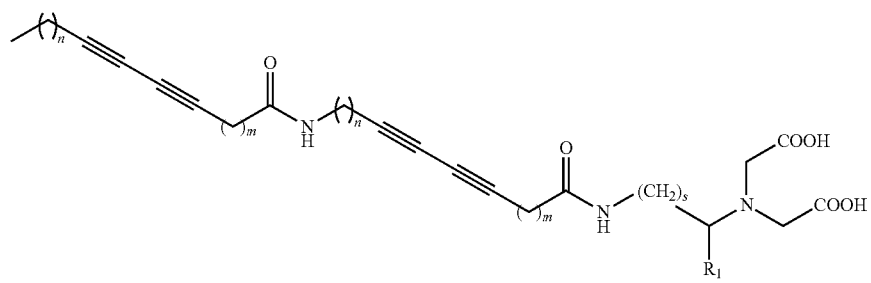

The polymerised micelles are also formed starting from polymerised amphiphilic molecules obtained starting from the amphiphilic molecule of formula

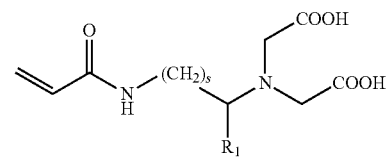

Preferably, the polymerised micelles according to the invention are composed of polymerised amphiphilic molecules obtained starting from the amphiphilic molecule of formula

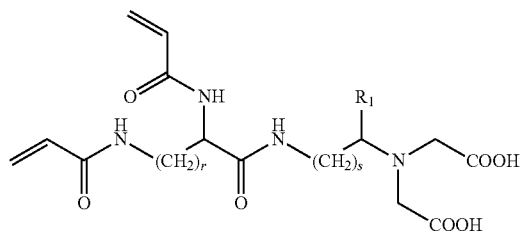

Preferably, the polymerised micelles are formed starting from polymerised amphiphilic molecules obtained starting from the amphiphilic molecule of formula

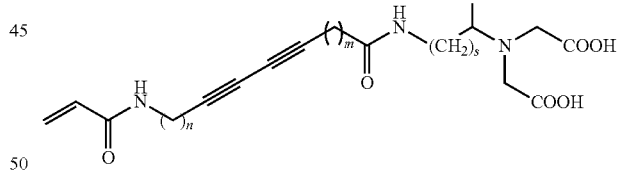

Advantageously, the polymerised micelles according to the invention are composed of polymerised amphiphilic molecules obtained starting from the amphiphilic molecule of formula

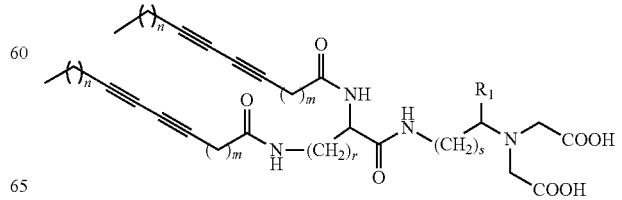

The present invention relates also to a process for the preparation of compounds according to the invention, which process is characterised in that:

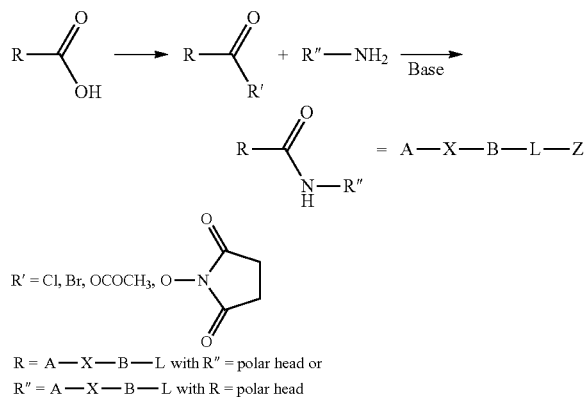

R = A—X—B—L with R" = polar head or
R" = A—X—B—L with R = polar head

The invention relates also to pharmaceutical compositions comprising polymerised micelles according to the invention.

Advantageously, these pharmaceutical compositions comprise one or more pharmaceutically acceptable excipients, i.e. one or more suitable, inert, non-toxic carriers or excipients.

As regards the pharmaceutically acceptable excipients, there may be mentioned, without implying any limitation, binders, diluents, disintegrating agents, stabilisers, preservatives, lubricants, fragrances, aromas or sweeteners.

Among the pharmaceutical compositions according to the invention, there will be more especially selected those that are suitable for administration by the oral, parenteral and especially intravenous, per- or trans-cutaneous, nasal, rectal, perlingual, ocular or respiratory routes, more specifically tablets or dragées, sublingual tablets, hard gelatin capsules, glossettes, capsules, lozenges, injectable preparations, aerosols, eye drops, nose drops, suppositories, creams, ointments or dermal gels.

The preferred route of administration is the intravenous route and the corresponding pharmaceutical compositions may allow instantaneous or deferred release of the active ingredients.

The present invention relates also to the use of polymerised micelles according to the invention as vectors of hydrophobic molecules.

The invention relates also to the use of polymerised micelles as vectors of hydrophobic active ingredients.

A "vector" is understood to be any molecule or assembly of molecules capable of transporting an active ingredient, a protein or a nucleic acid towards its site of action by targeting of specific ligands or, in passive manner, by solubilisation or stabilisation of the species in question.

An "active ingredient" is understood to be any molecule, protein or nucleic acid having a therapeutic effect.

Various methods of inclusion of active ingredients have been developed in order to optimise the level of inclusion or incorporation in the polymerised micelles. The methods of inclusion according to the invention are:
the "vortex" method, which consists of inclusion by means of vortex stirring of an aqueous solution of polymerised micelles and active ingredient in the powder state over about 30 minutes;
the "vortex/sonication" method, which consists of inclusion by means of vortex stirring combined with cycles of sonication of an aqueous solution of polymerised micelles and active ingredient in the powder state over about 2 hours;
the "stirring at 20° C." method, which consists of inclusion by magnetic stirring, at ambient temperature, over about 12 hours, of an aqueous solution of polymerised micelles and active ingredient in the powder state;
the "stirring at 50° C." method, which consists of inclusion by magnetic stirring, at about 50° C., over about 12 hours, of an aqueous solution of polymerised micelles and active ingredient in the powder state;
the "DCM evaporation" method, which consists of inclusion by adding active ingredient solubilised in dichloromethane (DCM) to an aqueous solution of polymerised micelles which is heated to about 50° C.

At the end of the inclusion sequence, the solution is filtered in order to remove the excess of non-included active ingredient.

The invention relates preferably to a method of inclusion by magnetic stirring, over 12 hours, at 50° C., of a solution of polymerised micelles and active ingredient. The inclusion of active ingredient in the polymerised micelles is controlled by the vigour of stirring and the temperature. The level of incorporation is improved by more vigorous stirring, by being in contact for longer and by a higher temperature.

Preferably, the micellar solutions obtained at the end of the inclusion step are sterilised by filtration through a 0.22-μm filter with a view to intravenous injection, without loss of active ingredient concentration.

The inclusion study carried out on the micelles has demonstrated the effect of polymerisation of the micelle on the active ingredient incorporation capability. The micelles must be polymerised in order for this nano-vector to have the capability of including very large amounts of active ingredient. A level of incorporation of S39625 of 48% is obtained for this transporter, which is a level 5 times greater than that obtained with the nano-ring formulation.

The inclusion study carried out on various active ingredients has confirmed the ability of this nano-vector to solubilize various types of hydrophobic molecules with high inclusion levels. The work conducted with a reference molecule, paclitaxel, has allowed the values for the levels of incorporation to be compared with the data from the literature. Polymerised micelles of the amphiphilic II-4 allowed the paclitaxel to be included at an inclusion level of 33%. In the literature, paclitaxel inclusion levels of between 6.7% and 14.3% inclusive have been reached with various types of vesicles, incorporation levels of between 0.2% and 27% inclusive with nanoparticles, and inclusion levels of between 0.2 and 25% inclusive with polymer micelles. The polymerised micelles therefore present themselves as a nano-vector having a remarkable power of solubilisation which has made it possible to solubilize active ingredients of various structures and molecular weights.

The present invention relates finally to a process for obtaining polymerised micelles according to the invention. This obtaining process comprises the following steps:
the lipid compounds to be polymerised in accordance with the invention are self-assembled into spherical micelles;
the self-assembled spherical micelles are polymerised.

"Self-assembly" of amphiphilic molecules is understood to be the spontaneous organisation, into spherical micelles, of amphiphilic molecules in aqueous media at a concentration greater than the critical micellar concentration or CMC.

The critical micellar concentration of the amphiphilic molecule II-4 as described hereinbefore was determined in experiments to be 0.082 mg/ml.

The invention relates also to a process for obtaining polymerised micelles, in which process the polymerisation step is of a light-irradiation or photopolymerization type.

Photopolymerization is a polymerisation method especially well suited to the polymerisation of diacetylene moieties. Photopolymerization is a "clean" method using irradiation with light at 254 nm and no external chemical agent. The photopolymerization of diacetylene moieties involves the formation of diradical intermediates: the first step consists of forming the diradical species by photon excitation; the second step is the reaction of propagation of the radical with a new polymerisable moiety located in proximity, thereby causing the polymer chain to grow; the last step is a step of termination by coupling of two radicals.

The invention relates also to a process for obtaining polymerised micelles, in which process the polymerisation step is of a free radical polymerisation type.

Vinyl and acrylate moieties are generally polymerised by free radical polymerisation. This polymerisation route is known and commonly used. Initiation of free radical polymerisation may be brought about with the aid of a free radical initiator generated by thermal and homolytic dissociation, by redox reaction or by irradiation.

Finally, the invention relates also to a process for obtaining polymerised micelles, in which process the polymerisation step comprises a plurality of types of successive polymerizations, for example photopolymerization and then polymerisation by means of a free radical initiator.

The present invention is illustrated by the following Examples, without being limited thereby.

Example 1

Synthesis of the Amphiphilic Molecules II-4 and II-23

1.1 Synthesis of the Amphiphilic Molecule II-4

The first step of this synthesis, in accordance with Scheme 1, consists of preparing the hydrophilic part of the amphiphilic molecule (nitrilotriacetic acid derivative) starting from N-benzyloxycarbonyl-L-lysine (Z-L-lysine).

Scheme 1:

Scheme 1:

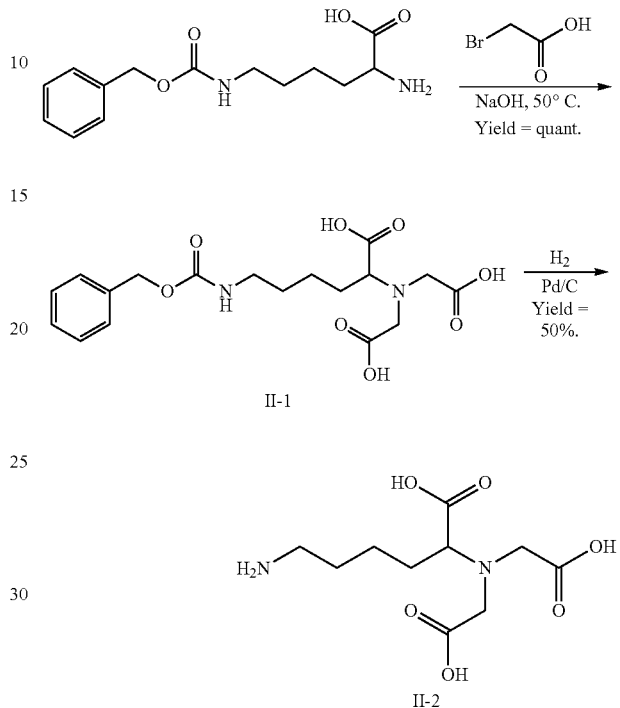

The second step of the synthesis, in accordance with Scheme 2, consists of coupling the hydrophilic head II-2 with previously activated 10,12-pentacosadiynoic acid.

Scheme 2:

The pentacosadiynoic acid is activated by N-hydroxysuccinimide in the presence of N-(3-dimethylaminopropyl)-N'-ethylcarbodiimide to yield the activated acid II-3. The surface-active agent II-4 is obtained by peptide coupling between the NTA hydrophilic head II-2 and the activated acid II-3. The pure product is obtained by precipitation from water by addition of hydrochloric acid.

1.2 Synthesis of the Amphiphilic Molecule II-23

The amphiphilic molecule II-23 is a surfactant having two types of polymerisable moieties: a diacetylene moiety polymerisable by irradiation with light at 254 nm and an acrylate moiety crosslinkable by electron bombardment.

The first synthesis step consists of preparing the hydrophilic part of the amphiphilic molecule (NTA head) starting from N-benzyloxycarbonyl-L-lysine (Z-L-lysine) in accordance with Scheme 1 and then protecting the carboxylic acids in the form of tert-butyl esters. There is obtained the protected hydrophilic head tBu-NTA designated II-14.

The second step of the synthesis is summarized in the following Reaction Scheme 3.

Scheme 3:

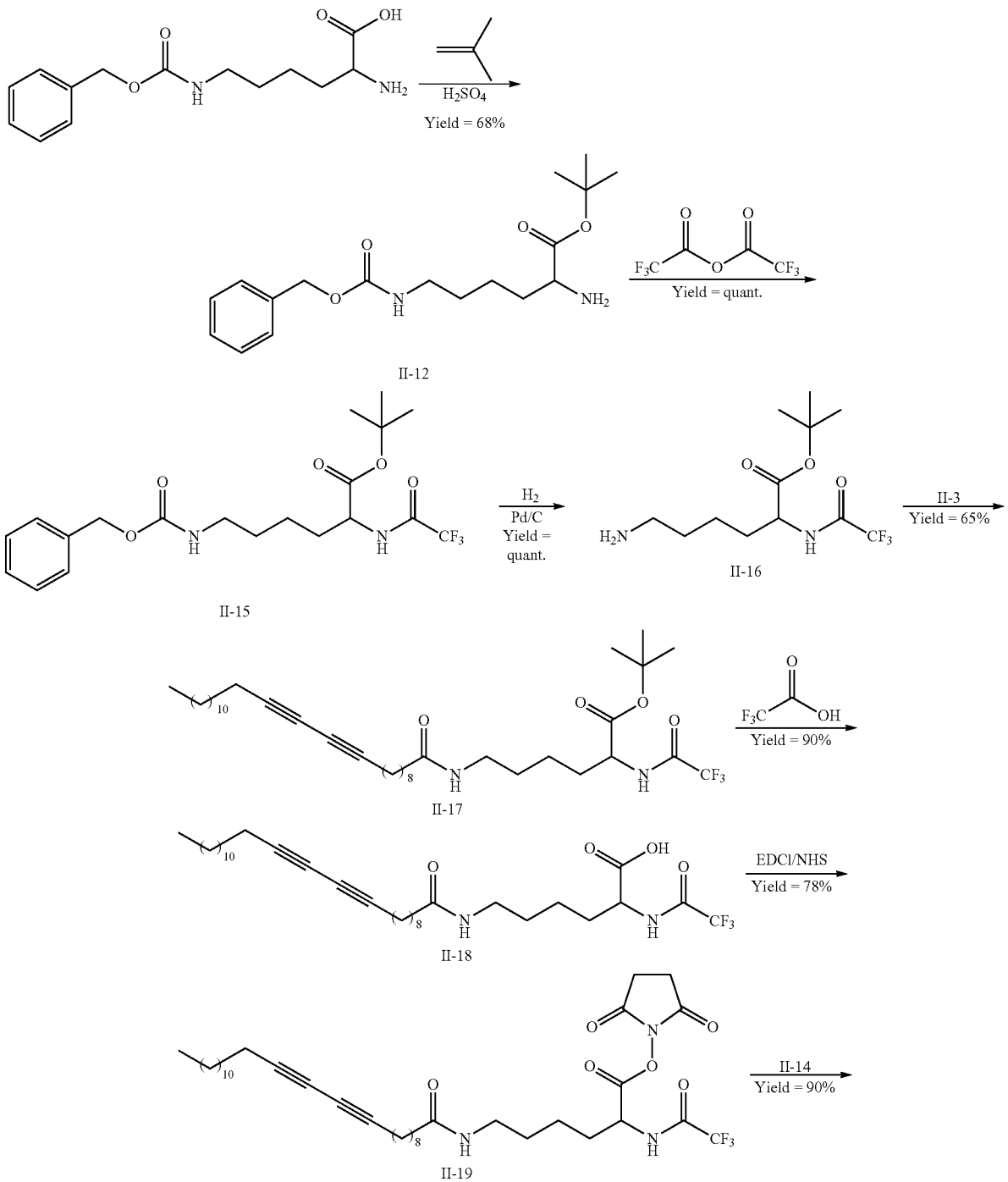

-continued
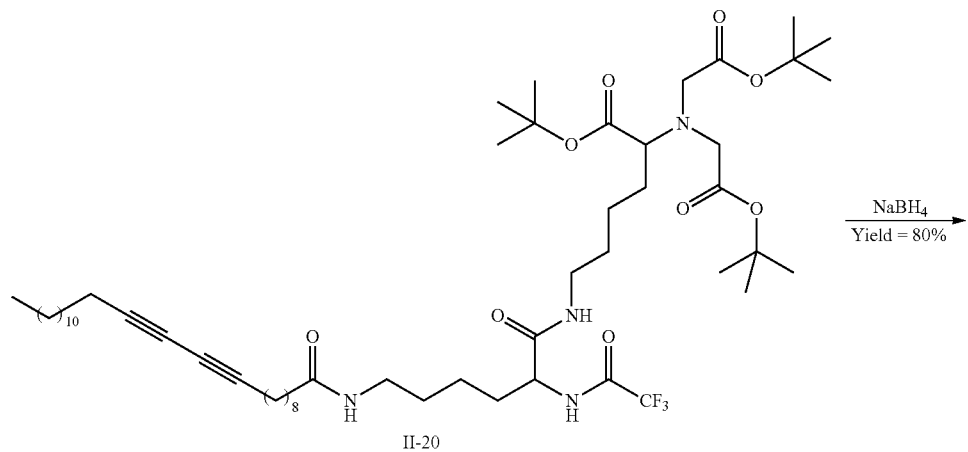
II-20
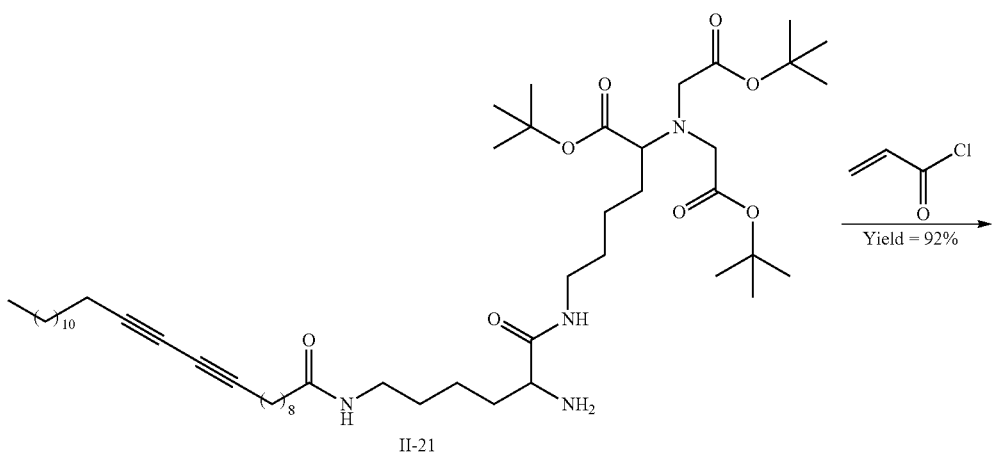
II-21
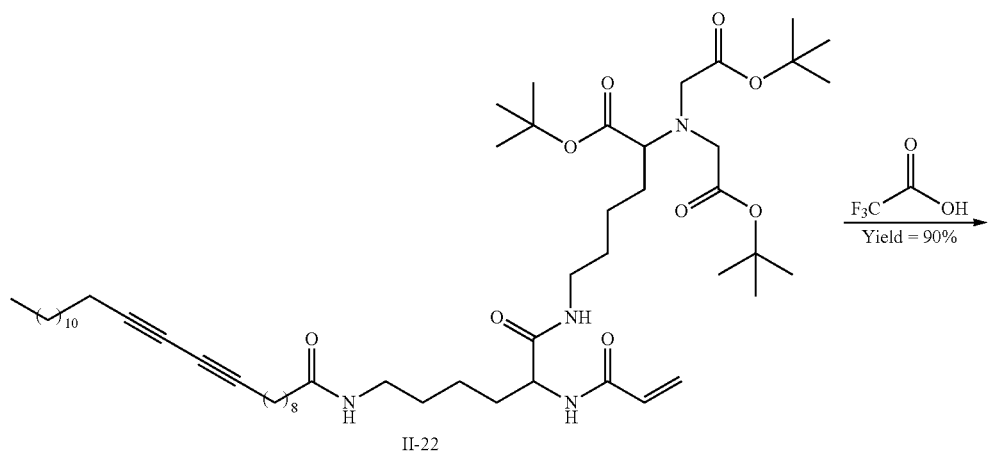
II-22

-continued

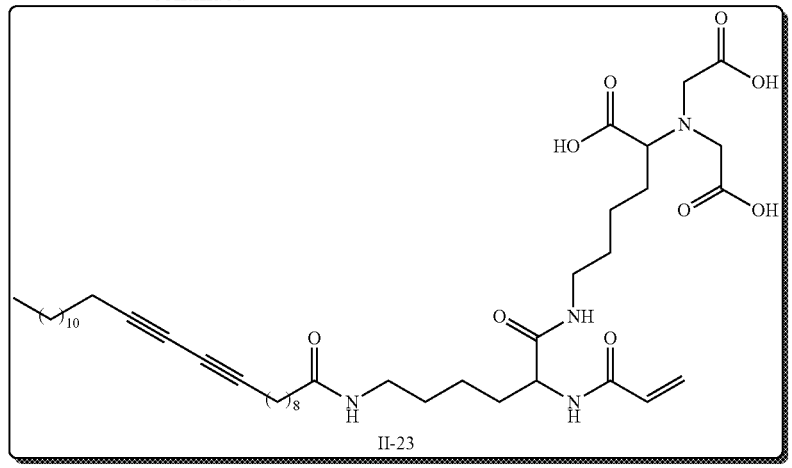

II-23

Example 2

Preparation and Characterisation of Polymerised Micelles 2.1 Preparation of Polymerised Micelles Spherical micelles are arrangements of amphiphilics obtained at and beyond the critical micellar concentration (CMC). These organised structures of spherical shape have a hydrophilic surface and a lipophilic or hydrophobic core.

The surface-active agent II-4 arranges itself in the form of spherical micelles when the pH of the aqueous solution is greater than 10. Beyond pH=10, the lone pair of the tertiary amine of the hydrophilic part of the surfactant is liberated, leading to an increase in the volume of the polar head, and below that pH value hydrogen bonds may form between the carboxylates and the hydrogen of the protonated tertiary amine, leading to a decrease in the volume of the HTA head of the amphiphilic II-4.

Figure 9:
FIG. 9 shows Scheme 4 illustrating the preparation of self-assembled and polymerised micelles of the amphiphilic II-4.

The self-assembled and polymerised micelles of the amphiphilic II-4 are prepared in accordance with Scheme 4 by irradiation, with light at 254 nm, of an aqueous solution of II-4 at pH=12 for 5 hours and then the pH is adjusted to physiological pH by dialysis against a solution having a pH between 7 and 8 inclusive (as shown in FIG. 9).

It is observed that polymerisation, by light irradiation, of the amphiphilic II-4 structured into the form of micelles is a relatively slow process and conversion of the entirety of the amphiphilics II-4 into polydiacetylene should be reached for polymerisation times beyond 5 hours.

2.2 Characterisation of the Polymerised Micelles

Analysis of the polymerised micelles of amphiphilics II-4 is carried out by means of laser particle size analysis. This technique, which is based on quasi-elastic light scattering and photon cross-correlation spectroscopy, makes it possible to determine the size distribution of a sample.

Intensity analysis of a sample of polymerised micelles at 50 mg/ml by the Nanophox apparatus shows a main population peak at 4.9 nm. Number analysis of the sample of polymerised micelles at 1 mg/ml by the Malvern Zetasizer apparatus has demonstrated the presence of a single population at 5.1 nm.

Polymerisation of the micelles causes a phenomenon of contraction of the micelles, which may be explained by the fact that the polymerisation fixes the assembly of amphiphilics and limits the swelling phenomena.

Example 3

Figure 2:
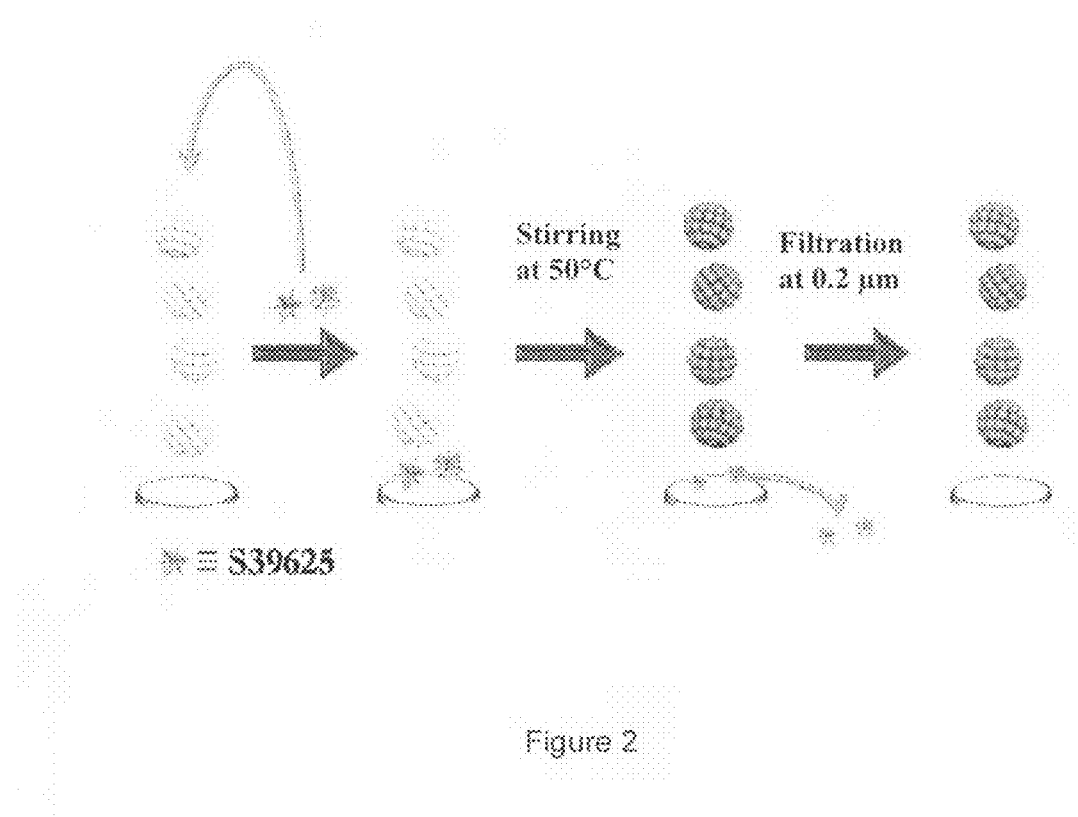
FIG. 2: Method of inclusion of S39625 in polymerised and non-polymerised micelles.

Inclusion of S39625 in Polymerised Micelles and in Non-Polymerised Micelles 3.1 Method of S39625 Inclusion S39625 was encapsulated in a solution of 10 mg/ml of non-polymerised micelles and of polymerised micelles by the "stirring and heating at 50° C." method as detailed in the description and shown in FIG. 2.

3.2 Determination of the Level of Inclusion of S39625, by HPLC

The level of inclusion of S39625 is determined by the reverse-phase HPLC method. This technique is based on the difference in the interaction of molecules between the mobile phase and the stationary phase. This difference affects the retention times for those molecules. For given HPLC conditions, the same molecule always has the same retention time. The reverse-phase HPLC conditions for determination of the level of inclusion of S39625 are an RP-18$^c$ grafted silica column for the stationary phase and a gradient of water and of acetonitrile from 5% to 100% for the mobile phase. Detection of the S39625 at the column exit is carried out by a UV detector at a wavelength of 385 nm. A standard curve for S39625 in acetonitrile was produced by reverse HPLC. Under these HPLC conditions, the active ingredient S39625 has a retention time of 25.8 minutes.

The retention time for S39625 encapsulated in polymerised micelles was also determined by reverse-phase HPLC for which the solvent gradient is replaced by an isocratic regime of pure acetonitrile. Acetonitrile is one of the better solvents of S39625 and its use as eluant makes it possible to ensure very rapid release of the active ingredient and its elution as a free entity.

3.3 Results for the Level of Inclusion of S39625

Figure 3:
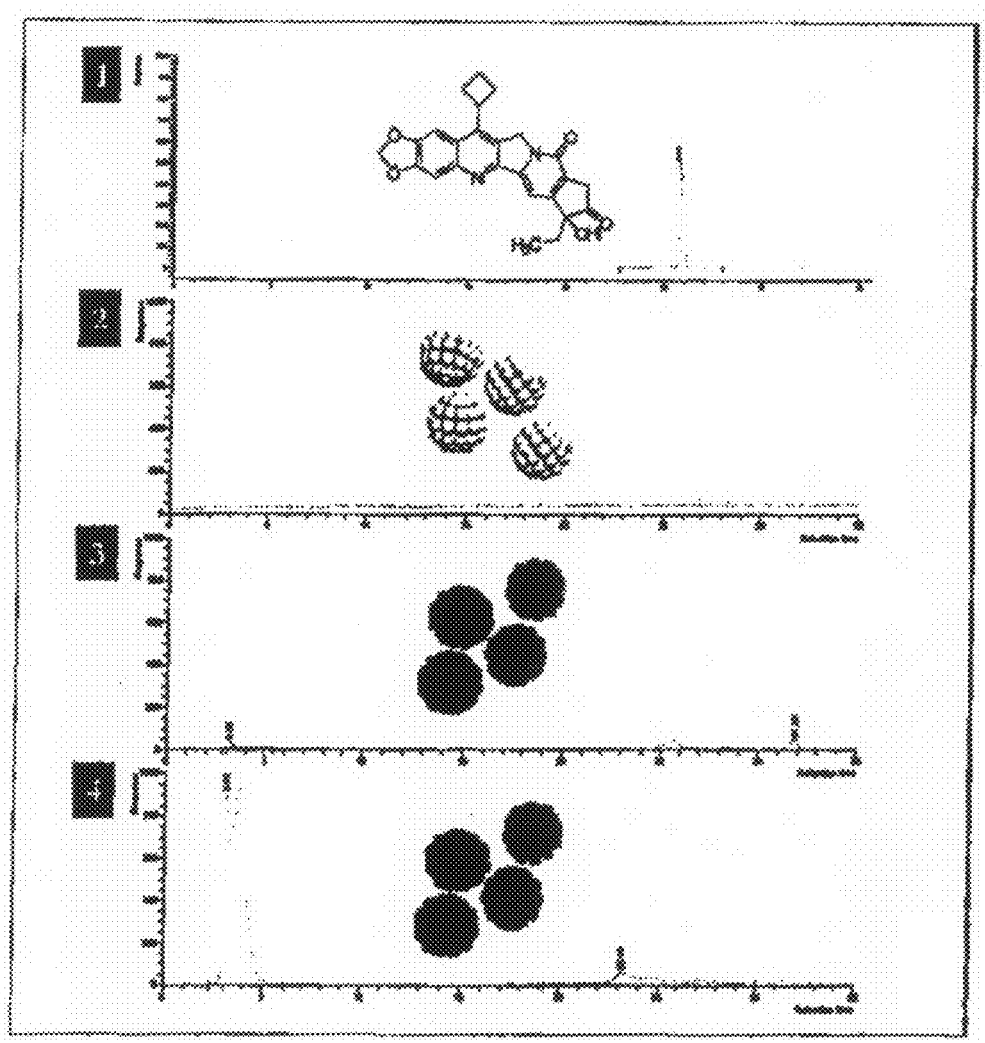
FIG. 3: (1) chromatogram of S39625 in acetonitrile, (2) chromatogram of non-polymerised/polymerised micelles, (3) chromatogram of S39625 included in non-polymerised micelles, (4) chromatogram of S39625 included in polymerised micelles.
Figure 4:
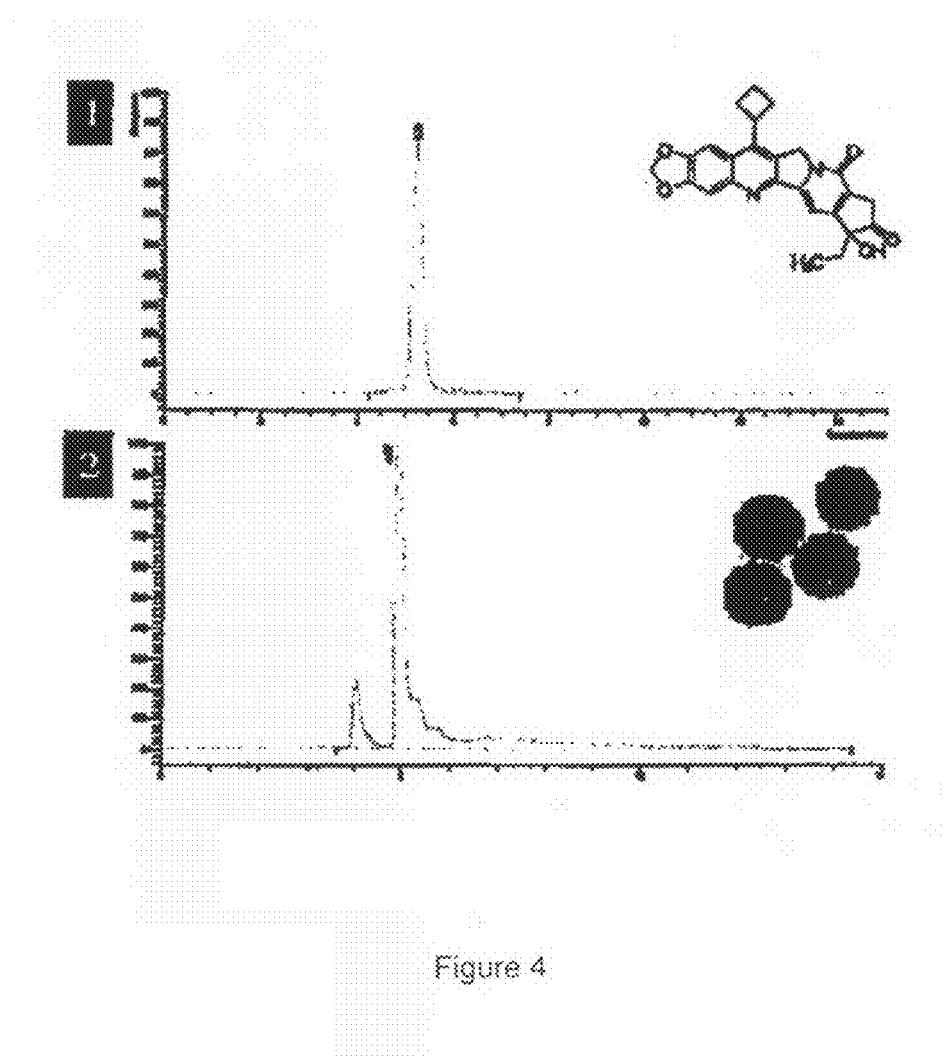
FIG. 4: (1) chromatogram of S39625 solubilised in acetonitrile, (2) chromatogram of S39625 included in polymerised micelles.

The results for incorporation of S39625 are calculated starting from FIG. 3.

The chromatogram of S39625 included in non-polymerised micelles shows the three peaks at 3.2 minutes, 25.8 minutes and 31.9 minutes. On the basis of the area of the peak at 25.8 minutes, incorporation of the active ingredient in non-polymerised micelles is between 1.7 and 3.3% inclusive.

The chromatogram of S39625 included in polymerised micelles shows a wide peak at a very short retention time. This marked decrease in retention time shows, on the one hand, that the hydrophobicity of S39625 is greatly masked by the very hydrophilic surface of the polymerised micelle and, on the other hand, that the S39625/polymerised micelle association is especially robust.

The chromatogram of S39625 solubilised in acetonitrile has a peak at 5.2 minutes whereas S39625 included in the polymerised micelle has two peaks at 4.0 and 4.9 minutes. The level of inclusion of S39625 and its degradation products in the polymerised micelles is estimated by integration of the two peaks. The level of incorporation of these molecules in the polymerised micelles is therefore 48%. For the same concentration of amphiphilic (10 mg/ml), the solubility and therefore the encapsulation capability of the polymerised micelles is improved by a factor of 5 relative to nano-rings and by a factor of 13 relative to non-polymerised micelles.

Example 4

Inclusion of Hydrophobic Active Ingredients in Polymerised Micelles

Figure 5:
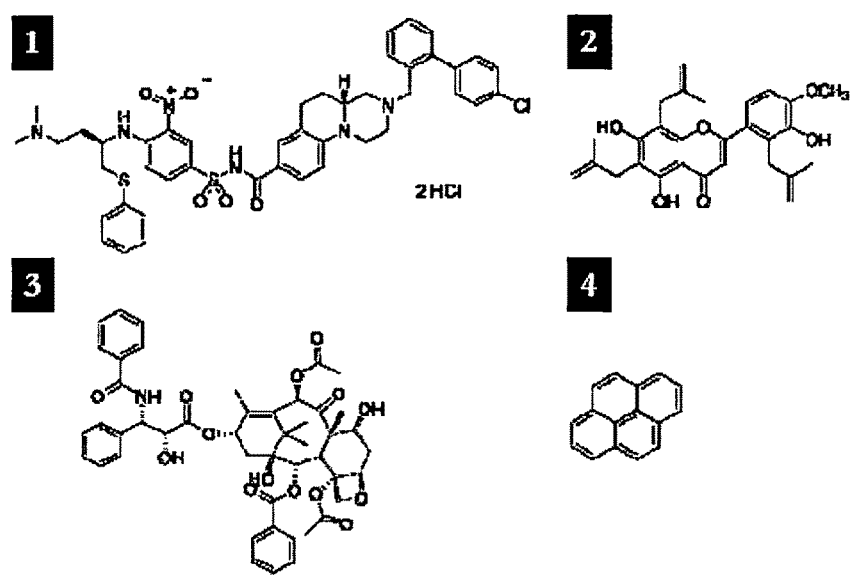
FIG. 5: Structures of the hydrophobic active ingredients (1) S44563, (2) 42909, (3) paclitaxel and (4) pyrene.

Inclusion tests are carried out on the hydrophobic active ingredients S42909 and S44563, on paclitaxel, a reference hydrophobic active molecule, and on pyrene, a very hydrophobic molecule. The chemical formulae of these hydrophobic active ingredients are shown in FIG. 5. Inclusion of these active ingredients was carried out using solutions of polymerised micelles at 10 mg/ml by the method of heating at 50° C. for 12 hours.

All of the results in Table 1 show substantial incorporation of the hydrophobic molecules in the polymerised micelles, with levels of inclusion greater than 24% and an increase in the solubility of the active ingredients in water of 30 000 to 500 000.

TABLE 1

| Active ingredient molecule | Molecular weight (g/mol) | Solubility of the molecule in water (in μg/mL) | Level of inclusion by weight$^f$ (in %) | Molar level of inclusion$^g$ (in %) | Number of molecules per micelle$^h$ | Solubility in water (in mg/mL) |
|---|---|---|---|---|---|---|
| S 39625 | 430 | 0.09 | 48 | 56 | 125 | 9.00 |
| S 44563 | 912 | 2.00 | 45 | 36 | 56 | 8.30 |
| S 42909 | 462 | 0.20 | 24 | 29 | 42 | 3.15 |
| Paclitaxel | 853 | 0.40 | 31 | 25 | 33 | 4.55 |
| Pyrene | 202 | 0.01 | 34 | 63 | 167 | 5.25 |

$^f$Weight ratio (in %) between medicament and medicament + transporter × 100 in the formulation after treatment
$^g$Molar ratio (in %) between medicament and medicament + amphiphilic II-4 × 100 in the formulation after treatment
$^h$Molar ratio between medicament and amphiphilic II-4 × number of amphiphilics/micelle (100 molecules)

Example 5

Figure 6:
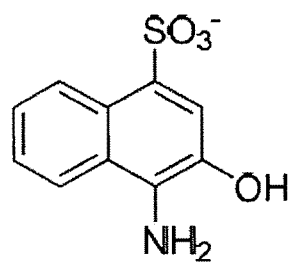
FIG. 6: Chemical structure of 4-amino-3-hydroxynaphthalene-1-sulphonate.

Functionalisation of Polymerised Micelles 5.1 Functionalisation by 4-amino-3-hydroxynaphthalene sulphonate Polymerised micelles are functionalised by a hydrophilic fluorophore, 4-amino-3-hydroxynaphthalene sulphonate, described in FIG. 6. This fluorophore has an excitation wavelength of 340 nm and an emission wavelength of 455 nm.

Attachment of the fluorophore is carried out by peptide coupling in water at basic pH (pH=12) using dicyclohexylcarbodiimide (DCC) as coupling agent. This grafting was carried out in a large excess of fluorophore (50 equivalents) and coupling agent (100 equivalents), and the samples were purified by means of a size exclusion column.

Figure 7:
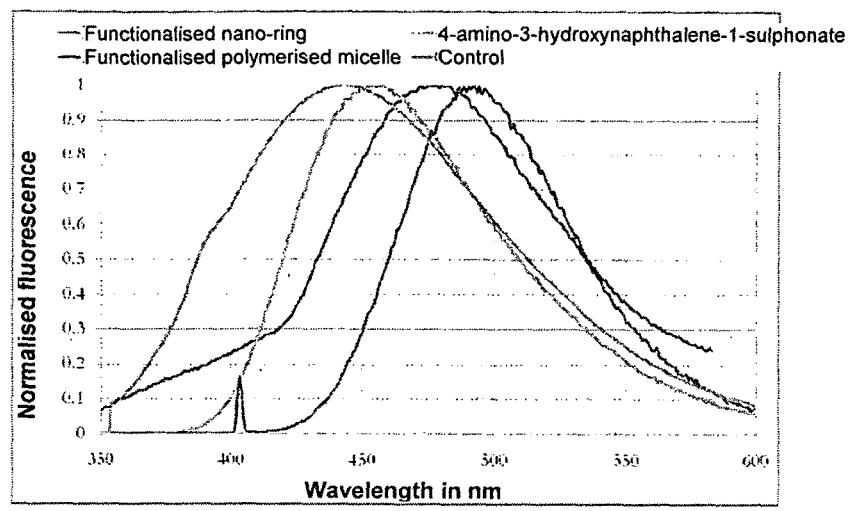
FIG. 7: Fluorescence spectra of 4-amino-3-hydroxynaphthalene-1-sulphonate, of nano-rings and polymerized micelles functionalised with the fluorophore, and of the control sample (excitation at 345 nm).

Functionalisation of the polymerised micelles was followed by fluorescence spectroscopy in order to demonstrate grafting of the fluorophore to the surface of the nano-vector. The fluorescence spectra of the functionalised polymerised micelles show a change in the fluorescence peak of 4-amino-3-hydroxynaphthalene sulphonate with a bathochromic fluorescence shift at 492 nm (FIG. 7). The control demonstrates that the fluorescence shift of the polymerised micelles is indeed due to the covalent grafting of the fluorophore onto the surface of the nano-vector.

5.2 Functionalisation by Folic Acid

As the folate receptor is overexpressed on the surface of cancerous cells, folic acid is very widely used for the specific targeting of cancerous cells of the brain, kidneys, breasts, ovaries and lungs.

In order to carry out the step of coupling the folic acid to the polymerised micelles, folic acid was modified in order to introduce an amine function allowing grafting. Coupling of the amine derivative of folic acid III-9 to the surface of polymerised micelles is carried out by peptide coupling in water at a basic pH (pH=12) using DCC as coupling agent. This grafting is carried out in a large excess of the amine derivative of folic acid (50 equivalents) and of coupling agent (100 equivalents). The sample was purified by filtration and then by means of a size exclusion column.

Figure 8:
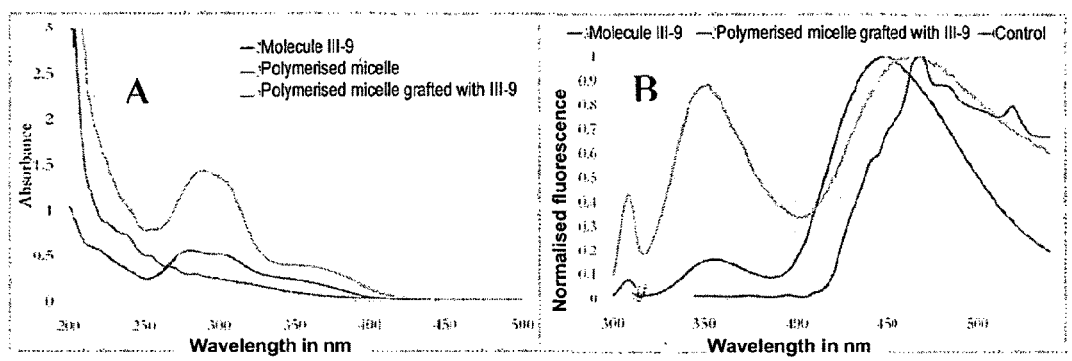
FIG. 8: (A) absorbance spectra of the amine III-9, of polymerised micelles, and of polymerised micelles functionalized with the amine III-9 (B) fluorescence spectra of the amine III-9, of polymerised micelles functionalised with the amine III-9, and of the control sample (excitation at 280 nm).

The absorption spectra of FIG. 8 show that the amine derivative of folic acid III-9 is indeed present on the surface of the polymerised micelles by virtue of the fact of the presence of the peak at 285 nm. The fluorescence spectra of functionalised polymerised micelles show a change in the fluorescence peaks of the amine derivative of folic acid at 360 nm and 450 nm.

5.3 Functionalisation by PEG

The potential phagocytosis of the micelles of nanometric size according to the invention by macrophages may be avoided by grafting chains of PEG, or PolyEthylene Glycol, onto these micelles. The presence of PEG on the surface of the micelles creates an inert outer layer preventing the adhesion of opsonins, therefore providing said micelles with properties of stealth vis-a-vis the macrophages and thereby increasing their circulation time in the blood pool.

Coupling a methoxyPEG-amine 5000 to the surface of the polymerised micelle is carried out at pH 12 using DCC as coupling agent. This grafting is carried out in a large excess of PEG derivative (25 equivalents) and of coupling agent (100 equivalents). The derivatised micelles are purified by filtration followed by a size exclusion column.

Example 6

Toxicological Study of the Polymerised Micelles

The distribution of the polymerised micelles within the body is a very important parameter to be tested in order to determine the mode of excretion and the mode of accumulation of said polymerised micelles.

In order to carry out this study, the amphiphilic II-4 is radio-labelled with carbon 14 so as to synthesise the radio-labelled polymerised micelle for an autoradiographic tracking study in the rat. The amphiphilic radio-labelled with carbon 14 is obtained with a specific activity of 7.6 μCi/mg.

Administration of the polymerised micelles to the rat is carried out at a dose of 4 MBq/kg and 100 mg/kg for an administration volume of 2.5 ml/kg. For this, a 40 mg/ml solution is necessary with a specific activity of 7.6 μCi/mg.

The study of the accumulation/elimination of polymerised micelles radio-labelled with carbon 14 was carried out in 3 male rats of the Wistar type. A single dose of 100 mg/kg of polymerised micelles [$^{14}$C] was administered by the intravenous route (bolus) to each of the rats, and the animals were euthanized at 10 minutes, 24 hours and 48 hours. The urines of the 24 hour and 48 hour rats were collected in order to measure the activity thereof by liquid scintillation. Quantification of the levels of radioactivity in the tissues was carried out by radioluminography of specific sections of the rats obtained by cryomicrotomy.

Analysis of the radioluminograms of the 10 minute rat, i.e. the rat euthanized at 10 minutes, shows a generalised distribution of radioactivity in the body of the rat due to a high concentration of polymerised micelles in the blood. High levels of radioactivity were detected in certain tissues such as the lungs, the kidneys and the medullary substance thereof, the liver, the adrenal glands or the spleen.

Analysis of the radioluminograms of the 24 and 48 hour rats, i.e. the rats euthanized at 24 and 48 hours respectively, reveals a high concentration of radioactivity in the liver, the intestinal wall, the spleen, the adrenal glands, the kidneys and the bone marrow.

The invention claimed is:

1. Polymerized micelles comprising polymerized amphiphilic molecules, wherein the amphiphilic molecules are of the following general formula: A-X—B-L-Z, wherein
A represents $CH_3$—$(CH_2)_m$—C≡C—C≡C—$(CH_2)_n$— or $CH_2$=CH— or $CH_2$=CH—$C_6H_4$—,
n and m, which may be the same or different, are integers from 1 to 16;
X represents CO—NH, NH—CO, a bond or is absent;
B represents —$(CH_2)_m$—C≡C—C≡C—$(CH_2)_n$—, —CH=CH—$C_6H_4$—, or is absent, n and m, which may be the same or different, are integers from 1 to 16;
L represents —$(CH_2)_r$—CH[NH—CO-A']-, or is absent, r is an integer from 1 to 16, and A' represents A;
wherein X is absent if B and L are absent; and
Z represents

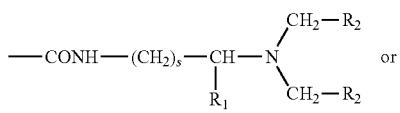

or

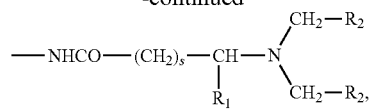

wherein s is an integer from 1 to 16, $R_2$ represents COOH, $SO_3H$, $OSO_3H$, $OPO_3H_2$, or $OPO_2H_2$, $R_1$ represents H, COOH, $SO_3H$, $OSO_3H$, $OPO_3H_2$, $OPO_2H_2$ or —CO—NH—$(CH_2)_t$—$CH_3$, wherein t is an integer from 1 to 16, or Z is a neutral hydrophilic sugar or a polysaccharide, or addition salts thereof with a pharmaceutically acceptable acid or base.

2. The polymerized micelles of claim 1,
wherein A represents $CH_3$—$(CH_2)_m$—C≡C—C≡C—$(CH_2)_n$—,
n and m, which may be the same or different, are integers from 1 to 16;
X represents CO—NH, NH—CO or is absent, B represents —$(CH_2)_m$—C≡C—C≡C—$(CH_2)_n$—, or is absent, n and m, which may be the same or different, are integers from 1 to 16;
L represents —$(CH_2)_r$—CH[NH—CO-A']-, or is absent, r is an integer from 1 to 16, and A' represents A or $CH_2$=CH— or $CH_2$=CH—$C_6H_4$—, wherein X is absent if B and L are absent; and
Z represents

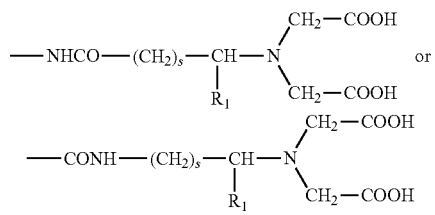

wherein s is an integer from 1 to 16, $R_1$ represents H, COOH, or —CO—NH—$(CH_2)_t$—$CH_3$, wherein t is an integer from 1 to 16, or Z is a neutral hydrophilic sugar or a polysaccharide, or addition salts thereof with a pharmaceutically acceptable acid or base.

3. The polymerized micelles of claim 1, wherein Z is functionalised.

4. The polymerized micelles of claim 3, wherein Z is functionalized by a folic acid.

5. The polymerized micelles of claim 1, further comprising one or more hydrophobic compounds.

6. The polymerized micelles of claim 1, wherein the polymerized amphiphilic molecules comprise an amphiphilic molecule II-4 of formula

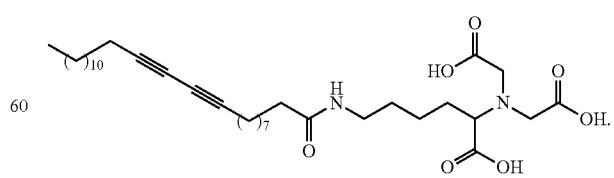

7. The polymerized micelles of claim 1, wherein the polymerized amphiphilic molecules comprise an amphiphilic molecule II-23 of formula

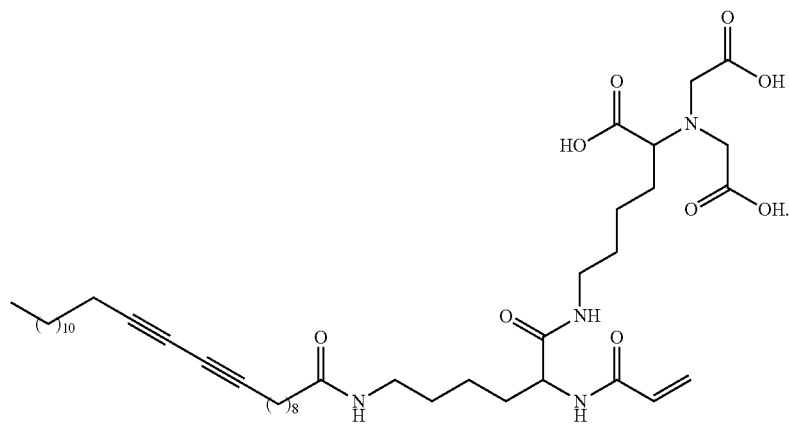

8. The polymerized micelles of claim 1, wherein the polymerized amphiphilic molecules comprise an amphiphilic molecule of formula

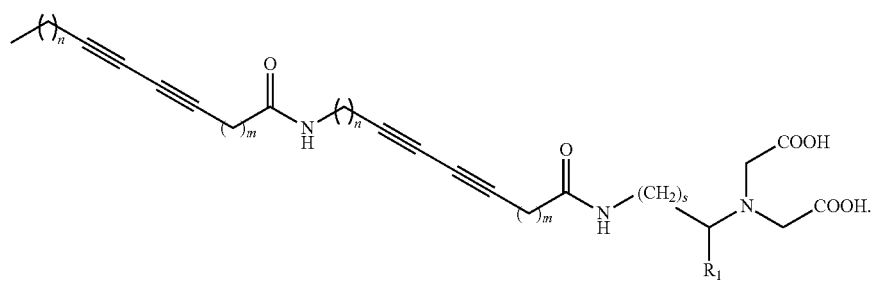

9. The polymerized micelles of claim 1, wherein the polymerized amphiphilic molecules comprise an amphiphilic molecule of formula

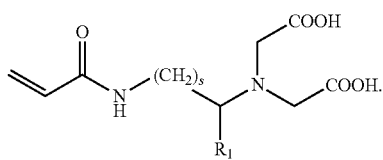

10. The polymerized micelles of claim 1, wherein the polymerized amphiphilic molecules comprise an amphiphilic molecule of formula

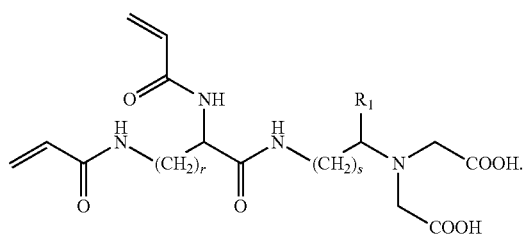

11. The polymerized micelles of claim 1, wherein the polymerized amphiphilic molecules comprise an amphiphilic molecule of formula

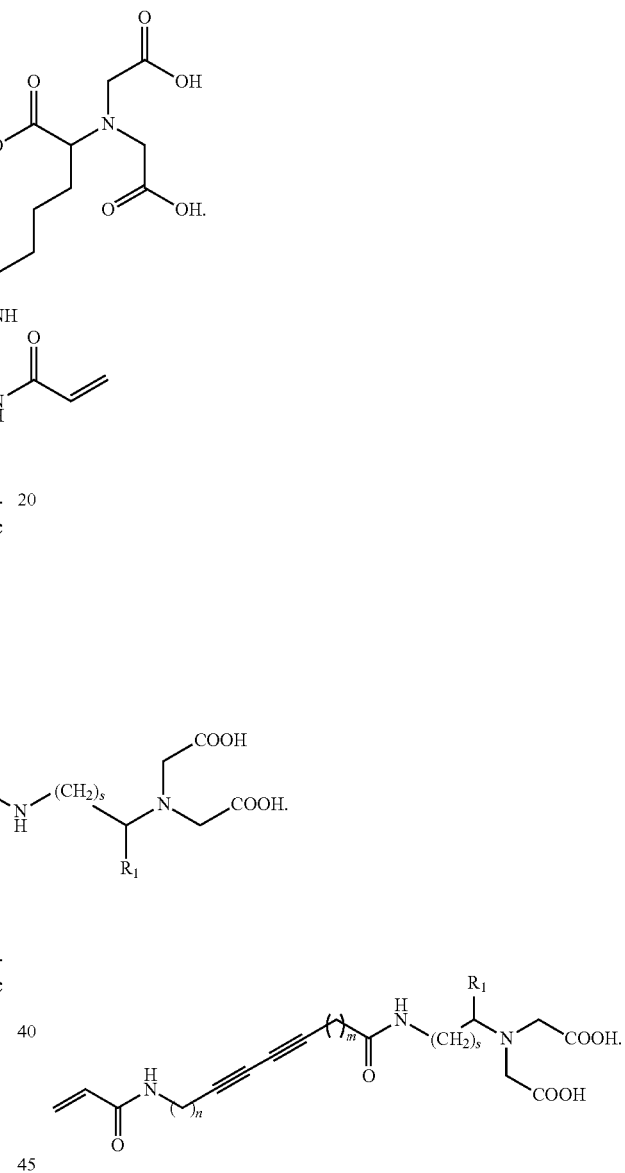

12. The polymerized micelles of claim 1, wherein the polymerized amphiphilic molecules comprise an amphiphilic molecule of formula

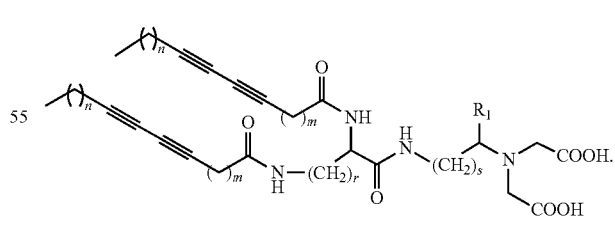

13. A composition comprising the polymerized micelles of claim 1.

14. The composition of claim 13, further comprising one or more pharmaceutically acceptable excipients.

15. A method of transporting an active ingredient toward its site of action comprising administering the polymerized micelles of claim 1 to a subject, wherein the polymerized micelles further comprise one or more hydrophobic active ingredients.

16. A process for obtaining the polymerized micelles of claim 1, comprising the following steps:
  i) combining the amphiphilic compounds to be polymerized, wherein the compounds are self-assembled into spherical micelles; and
  ii) polymerizing the self-assembled spherical micelles.

17. The process of claim 16, wherein the self-assembled spherical micelles are photopolymerized.

18. The process of claim 16, wherein the self-assembled spherical micelles are polymerized by free radical polymerization.

* * * * *

UNITED STATES PATENT AND TRADEMARK OFFICE
CERTIFICATE OF CORRECTION

PATENT NO.       : 8,663,660 B2                                   Page 1 of 1
APPLICATION NO.  : 12/736627
DATED            : March 4, 2014
INVENTOR(S)      : Julien Ogier et al.

It is certified that error appears in the above-identified patent and that said Letters Patent is hereby corrected as shown below:

On the Title Page, Item (73) Assignees: "Les Laboratories Servier" should be --Les Laboratoires Servier--.

In the Claims

Column 19, Line 53: "a bond or is absent" should be --or is absent--.

Column 20, Line 12: "sugar or a polysaccharide" should be --sugar or polysaccharide--.

Column 20, Line 42: "sugar or a polysaccharide" should be --sugar or polysaccharide--.

Signed and Sealed this
Twentieth Day of May, 2014

Michelle K. Lee
*Deputy Director of the United States Patent and Trademark Office*